United States Patent [19]

Cuff et al.

[11] Patent Number: 4,518,547

[45] Date of Patent: May 21, 1985

[54] MICROENCAPSULATION PROCESS

[75] Inventors: George W. Cuff, Indianapolis, Ind.; James W. McGinity, Austin, Tex.

[73] Assignee: Board of Regents, The University of Texas System, Austin, Tex.

[21] Appl. No.: 532,458

[22] Filed: Sep. 15, 1983

[51] Int. Cl.$^3$ .................. A61K 9/50; A61K 9/58; B01J 13/02

[52] U.S. Cl. ............................... 264/4.7; 8/526; 252/408.1; 424/22; 424/32; 428/402.21; 514/282

[58] Field of Search ............... 264/4.7; 427/213.34; 424/32

[56] References Cited

U.S. PATENT DOCUMENTS

| | | | |
|---|---|---|---|
| 3,575,882 | 4/1971 | Vandegaer | 264/4.7 |
| 3,886,084 | 5/1975 | Vassiliades | 428/402.2 X |
| 4,219,604 | 8/1980 | Kakimi et al. | 264/4.7 X |
| 4,251,386 | 2/1981 | Saeki et al. | 424/32 X |
| 4,309,213 | 1/1982 | Graber et al. | 71/120 |
| 4,322,311 | 3/1982 | Lim et al. | 264/4.7 |
| 4,324,683 | 4/1983 | Lim et al. | 264/4.7 X |

OTHER PUBLICATIONS

"Influences of Matrixes on Nylon-Encapsulated Pharmaceuticals", James W. McGinity, et al., Journal of Pharmaceutical Sciences, vol. 70(4), pp. 372-375 (1981).

"Semipermeable Aqueous Microcapsules", T. M. S. Chang, Canadian Journal of Physiology and Pharmacology, vol. 44, pp. 115-128 (1966).

George William Cuff, Dissertation: Physical-Chemical Characterization of Nylon Microencapsulated Pharmaceuticals.

Primary Examiner—Richard D. Lovering
Attorney, Agent, or Firm—Arnold, White & Durkee

[57] ABSTRACT

Nylon coated microcapsules containing hydrophilic solvent-soluble anionic, cationic or quaternary drug salts were prepared by interfacial polycondensation techniques. In a first stage, the drug substance to be encapsulated is dissolved in an aqueous phase. Examples of drugs encapsulated are morphine sulfate, diphenhydramine hydrochloride, and methantheline bromide. Next the aqueous drug solution is dispersed in an organic phase. In a second stage complementary polycondensation reactants each in an organic phase are added separately, either sequentially or simultaneously, to the dispersion prepared in the first stage. Microcapsules of nylon form around the hydrophilic solvent soluble core drug substance.

10 Claims, 2 Drawing Figures

MICROENCAPSULATION PROCESS

BACKGROUND OF THE INVENTION

The present invention relates to a process for microencapsulation of hydrophilic core materials utilizing interfacial polycondensation techniques.

The encapsulation of core substances by interfacial polycondensation has been widely used in the pharmaceutical, agricultural, dye, paint, and carbonless paper industries. Microencapsulation is a process whereby small particles of core materials such as liquids, solids, solutions, or dispersions are thinly coated by a separate material. Microencapsulation is often used to improve certain physical characteristic of formulations such as compressibility and flow. In addition, microencapsulation has been utilized to modify chemical release, to improve chemical stability, and to permit the mixing and storage of reactive or incompatible materials.

The principle of the microencapsulation method lies in bringing into contact a first liquid phase containing the core material to be encapsulated and a polycondensation reagent, with another liquid phase which is immiscible with the first phase and contains a second reagent capable of reacting with the first to give a polycondensation product. When the two phases are brought into contact, the two condensation reagents react at the interface of the phases, and by polycondensation, a wall of polymer forms around the drops of liquid core materials. The capsules obtained can then be washed and dried before use.

Various particular methods for carrying out this general technique have been proposed. One method consists of carrying out the dispersion and reaction simultaneously. For example, in a first stage, an aqueous phase is prepared which contains the core substance to be encapsulated generally dissolved in a solvent together with a hydrophilic polycondensation reagent. This first phase is then dispersed in an organic phase containing a hydrophobic polycondensation reagent. In this technique, the polycondensation reaction takes place at the actual moment of dispersion. Because the polycondensation and dispersion reactions occur simultaneously, microcapsules having an excessively wide distribution of diameters result.

In order to overcome this disadvantage, another technique features carrying out the process in two stages so as to separate the dispersion operation from the polycondensation reaction. For example, U.S. Pat. No. 3,522,346 to Chang, provides a process of encapsulating aqueous core substances in microcapsules having controlled size, thickness, and permeability. Droplets of an aqueous phase containing the core substance to be encapsulated together with the hydrophilic polycondensation reagent are dispersed in an organic phase. Next the hydrophobic polycondensation reagent is added to the dispersion thereby producing a polymerized microcapsule by interfacial condensation.

Initially polymer formation is rapid. However after the initial membrane is deposited, further polymerization is limited by the rate of diffusion of the hydrophilic polycondensation reactant into the organic solvent. Unfortunately as a consequence many of the microcapsules formed by this method are not easily recovered as a dry powder and tend to coalesce to form larger aggregates. Moreover, the encapsulated core substances are generally limited to anionic substances due to pH constraints of the aqueous phase.

In the utilization of interfacial polymerization techniques to encapsulate hydrophilic core materials, a particularly serious limitation has been encountered in the types of materials that are amenable to encapsulation. Specifically, the polycondensation monomer included in the aqueous phase poses certain pH constraints which affect the interfacial partitioning and pH stability of the selected core material to be encapsulated. For example, microencapsulation of quaternary drugs such as methantheline bromide and benzalkonium chloride has been heretofore generally unsuccessful. Further, microencapsulation of xanthine drugs and cationic drugs has generally resulted in low yield of encapsulated drug generally due to partitioning of the drug into the organic phase. In some instances degradation of the core material is observed and may be attributed to the pH conditions of the core influenced by residual monomer in the aqueous phase after polymerization is complete.

The problems discussed above can generally be attributed to the polycondensation monomer included in the aqueous phase to be microencapsulated. If the pH of the aqueous core can be controlled, then a much greater control over drug solubility, partitioning and stability can be established for the particular core material to be encapsulated. The present invention provides a process for microencapsulating a hydrophilic core material which overcomes many of the problems encountered with prior methods.

SUMMARY OF THE INVENTION

The present invention provides a process for the microencapsulation of a hydrophilic core material by interfacial polycondensation.

The process involves preparing, in a first stage, a dispersion of a continuous hydrophobic phase in a discontinuous hydrophilic phase containing the hydrophilic core material to be encapsulated. The hydrophilic core material is generally selected from chemically or biologically active substances. Such substances can be anionic, cationic, quaternary, or amphoteric salts as well as nonionic substances. Examples of materials to be encapsulated include drug substances, proteins, enzymes, living tissues or cells, inks, dyes, herbicides, etc.

In a second stage, interfacial polycondensation is induced by adding separately, either simultaneously or sequentially each of two complementary polycondensation monomers to the dispersion. One of the monomer components is a hydrophobic polycondensation reactant, for example multifunctional acid halides, diacids, diisocyanates and multifunctional sulfonyl halides and mixtures thereof. The other monomer component comprises a hydrophilic polycondensation reactant dispersed in a continuous hydrophobic solvent. Examples of hydrophilic polycondensation reactants include polyfunctional amines, polyols, diamines, diols, and other well known polycondensation system reactants.

Examples of some polymers formed by interfacial polymerization, which are useful in microencapsulation techniques of this invention include:

| POLYMER | MONOMERS | |
|---|---|---|
| | AQUEOUS-SOLUBLE | ORGANIC-SOLUBLE |
| polyamide | diamine | diacid halide |
| polyurethane | diamine | bischloroformate |
| polyurea | diamine | diisocyanate |

-continued

| POLYMER | MONOMERS | |
|---|---|---|
| | AQUEOUS-SOLUBLE | ORGANIC-SOLUBLE |
| polyester | glycol | diacid halide |
| epoxy resin | amine | epoxy resin |
| graft copolymer | casein | styrene/acrylonitrile |
| silicone | sodium trimethyl-silanolate | polymer of methyl-trimethoxysilane and dimethyl silicone |
| polyether | piperazine | 2,2'-dichlorodiethyl ether |
| polyphenyl-esters | bisphenol | acid dichloride |
| polyphthala-mides | diamine | phthaloyl dichloride |
| polyphenyl-phthalates | bisphenol | phthaloyl dichloride |

The monomers and resulting polymers are only representative and other may be substituted in many cases.

DETAILED DESCRIPTION OF PREFERRED EMBODIMENTS

Figure 1:
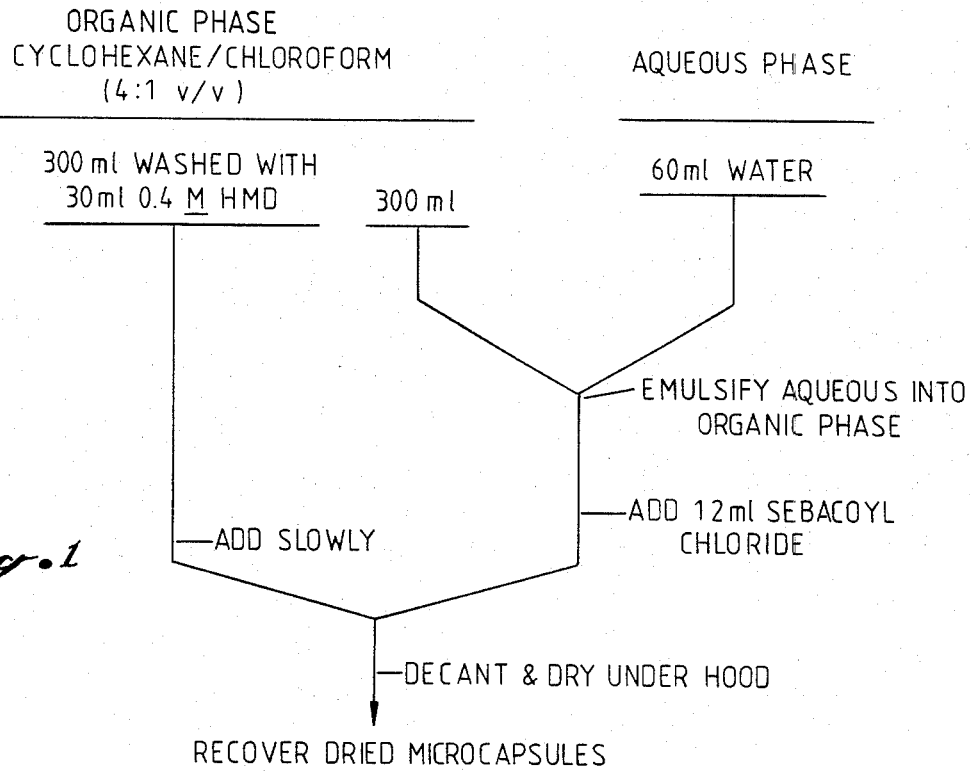
FIG. 1 represents a schematic diagram of an encapsulation method of this invention.

The invention will be described in terms of preferred embodiments which represent the best mode known to the Applicants at the time of this application.

The invention utilizes a variation in the well known microencapsulation technique known as interfacial polymerization. The system generally comprises two mutually immiscible solvents, one being hydrophobic, the other being hydrophilic or water. The hydrophilic solvent includes a hydrophilic core material to be encapsulated. A polymer system is selected of the type wherein two different monomers undergo a polyaddition or polycondensation reaction to form polymer chains comprising alternating monomer units. The two reactive monomers must accordingly be at least di-functional, although other polyfunctional monomers may be employed to increase the cross-link density of the finally formed membrane.

In view of the foregoing, it will be appreciated that a number of polymer systems are useable in the process of the invention. Thus, while this specification deals primarily with a polyfunctional amine-polyfunctional acid halide polymer system, the invention may also be practiced with, for example, polyols and diacid or diacid halide systems to produce polyester membranes; diamine and diisocyanate systems to produce a polyurea; diols and acid halides and diamines to produce polysulfonamides; and other well-known systems which react by polycondensation.

In the process of the invention, the core material to be encapsulated is dissolved in a hydrophilic solvent, e.g., water, preferably together with an inert carrier material such as gelatin, calcium sulfate, calcium alginate, polyvinylpyrrolidone, dextran, polyethylene glycol, ficol, hemoglobin, or albumin. The carrier material is selected to provide a suitable environment for the reactions which the chemically active material to be encapsulated undergoes. As a first dispersion, the hydrophilic or aqueous phase is mixed with a water immiscible organic solvent. As the two-phase system is dispersed, the hydrophobic solvent forms the continuous phase. The size of the droplets determines the size of the microcapsule which will be produced. Dispersion may be accomplished by any of the well known emulsification techniques such as, for example, using a blender, and may be accomplished with the aid of an emulsifying agent.

When droplets of a desired size have been produced, each of a hydrophobic solvent-soluble monomer and a second dispersion of hydrophilic solvent-soluble monomer in a hydrophobic phase is introduced into the first dispersion.

Polymerization occurs only at the interface of the two-phase system. If sufficient amounts of each monomer are added to the emulsion and the reaction is allowed to proceed to completion, capsule membranes are produced which vary in porosity, strength, and thickness, and it is difficult or impossible to control the reaction so that microcapsules of a given porosity or membrane thickness are produced.

In order that the invention may be more clearly understood, preferred embodiments will be further described in terms of the following examples, which should not be constructed to limit the scope of this invention.

EXAMPLE I

Microencapsulation was first approached by mechanically emulsifying 60 ml of water in 300 ml of organic solvent (chloroform/cyclohexane, 1:4). To this was added 150 ml of a 0.08 M solution of 1,6-hexamethylenediamine (HMD) in the organic solvent (corresponding to 30 ml of 0.4 M aqueous HMD) and 150 ml of the organic solvent containing 1.2 ml of sebacyl chloride (SC). The SC was added first. When the HMD was added, slowly at first and then more rapidly, a mass of nylon was recovered, and there was no indication that anything more than a few microcapsules had formed.

EXAMPLE II

A 30 ml of volume of 0.4 M aqueous HMD was washed with 300 ml of the organic phase (chloroform/cyclohexane, 1:4). The phases were separated and the organic phase was used as the source of HMD in an attempt to form nylon at an aqueous interface. Again, 60 ml of water was mechanically emulsified in 300 ml of the organic solvent. Then, 1.2 ml of SC was added to the stirred emulsion and the 300 ml of washed organic solvent was added very slowly at first and then more rapidly. Microcapsules were observed to form and no nylon was apparent in the organic solvent. This method is illustrated in FIG. 1.

EXAMPLE III

In order to determine if the present invention does in fact meet the goal of producing microcapsules containing an aqueous core not requiring an alkaline pH, a pH 4.0 buffer containing bromothymol blue indicator was encapsulated. Nylon microcapsules were produced as before in EXAMPLE II and there was no change in the color of the pH indicator. Therefore, an acidic aqueous phase was successfully microencapsulated and the pH of the aqueous media remained acidic throughout the entire process.

EXAMPLE IV

The present example demonstrates that the product encapsulated represents only microcapsules containing the desired aqueous media and that none of the microcapsules recovered are actually nylon fragments or other objects which may have been produced. These uncertainties were approached by microencapsulating an aqueous media to which ten drops of the water soluble dye, Adams' Food Color, Lot B-4 were added. When the microcapsules were prepared the dye was observed to remain only in the newly-formed nylon coated microcapsules and was not seen in the bulk organic solvent.

After the microcapsules were prepared, 3 samples were examined microscopically. Again, the dye was observed to remain entirely in the nylon microcapsules. There were no pieces of nylon or any dye observed that was not microencapsulated.

EXAMPLE V

To determine if partitioning of the dye as the unionized species might occur, aqueous buffer solutions which contained the dye were shaken with the organic phase. The pH range of the buffers was from 0.2 N HCl to 0.2 N NaOH. Three intermediate pH buffers and a solution of 0.4 M HMD were also equilibrated. The process of EXAMPLE II was repeated. In none of the cases was the dye observed to partition into the organic solvent or to diminish in the intensity of color.

EXAMPLE VI-X

Microcapsules were prepared containing no matrix material so that the aqueous microencapsulated media could be recovered and residual HMD determined. A variety of conditions of preparation were studied. In EXAMPLE VI, the prior art method of Chang et al. *Science*, 146:524 (1964) and of McGinity et al. *J. Pharm. Sci.* 64: 889 (1975) was used. An aqueous solution of 60 ml of 0.2 M HMD was emulsified in 300 ml of the organic solvent and a separate 300 ml portion of the organic solvent containing 1.2 ml of SC was added.

EXAMPLE VII involved preparation of the microcapsules by the method of the present invention described in FIG. 1 and EXAMPLE II-V. A volume of 60 ml of water was emulsified in 300 ml of the organic solvent. Then, 150 ml of organic solvent containing 1.2 ml SC was added, followed immediately by 150 ml of 0.08 M HMD dissolved in the organic solvent. The HMD was added slowly at first from a separatory funnel, then rapidly.

EXAMPLE VIII involved preparing microcapsules by the method of the present invention, but the concentration of HMD was 0.4 M. The method was the same as used in EXAMPLE VII otherwise.

EXAMPLE IX involved mechanically emulsifying 60 ml of water in 300 ml of the organic solvent. The SC and HMD (each in the organic solvent) were added simultaneously, from two separate infusion pumps. Therefore, this method of preparation will be referred to as the SAR (Simultaneous Addition of Reactants) method of interfacial polymerization. Each Harvard infusion pump held one 50 ml glass syringe with Teflon tubing leading into the sealed system. Both syringes were driven at about 2 ml/min for 30 seconds, then 15 ml/min for 30 seconds and then the remainder was delivered at 38 ml/min. One syringe contained 1.2 ml SC dissolved in a total of 50 ml of the organic solvent. The other syringe contained 50 ml of 0.08 M HMD in the same solvent.

EXAMPLE X was carried out identical to EXAMPLE IX except that the HMD concentration was $7.2 \times 10^{-2}$ M. This corresponded to the same amount of HMD present in 300 ml of organic solvent washed with 30 ml of 0.4 M aqueous HMD.

Table 2 outlines the duplicate results obtained for conditions VI through X:

| Example | Total Solvent Volume | HMD[1] (moles) | pH of[2] Media | HMD Concentration in core |
|---------|---------------------|----------------|----------------|---------------------------|
| VI | 600 ml | $12.0 \times 10^{-3}$ | 9.01 | $1.65 \times 10^{-2}$ M |
| VII | 600 ml | $12.0 \times 10^{-3}$ | 9.90 | $4.40 \times 10^{-2}$ M |
| VIII | 600 ml | $6.05 \times 10^{-3}$ | 4.05 | $6.3 \times 10^{-3}$ M |
| IX | 400 ml | $3.60 \times 10^{-3}$ | 2.73 | $8.30 \times 10^{-4}$ M |
| X | 400 ml | $4.00 \times 10^{-3}$ | 2.51 | $9.80 \times 10^{-4}$ |

[1]1.2 ml of SC ($5.626 \times 10^{-3}$ moles) was used in each case.
[2]pH after microcapsules were ruptured and diluted to 250 ml.

In EXAMPLE VI the pH of the aqueous phase after the microcapsules were ruptured and diluted to 250 ml was 9.01. This alkaline pH indicated that residual HMD was present in the core of the microcapsules. This was confirmed by the determination of $1.65 \times 10^{-2}$ M HMD inside the microcapsule core (corrected for dilution to 250 ml).

Unexpectedly, twice the concentration of HMD was found in EXAMPLE VII than in EXAMPLE VI.

Determination of HMD in the core of microcapsules under EXAMPLE VIII demonstrated considerably less of the HMD to be present. The total concentration of HMD was half that used in EXAMPLE VII, but the recovery of HMD from the core was about seven times less. Thus, the concentration of residual HMD in the microcapsule core is not a linear function of the original concentration of HMD.

Under EXAMPLES IX and X, a considerable decrease of the residual HMD in the microcapsule core occurred. This is a result of less of the HMD being added to the system. Also, the total organic solvent volume was reduced from 600 ml to 400 ml. Further, the controlled addition of reactants may contribute to the decrease in the HMD remaining in the final product. The pH of the aqueous media for EXAMPLE IX and X was very low, and is a result of HCl being generated by the polycondensation reaction.

Microcapsules produced by the methods described under EXAMPLES IX and X were not recovered as dry free-flowing powders. Therefore microcapsules were prepared which contain a core of either formaldehyde-crosslinked gelatin, calcium sulfate or calcium alginate.

EXAMPLE XI

Figure 2:
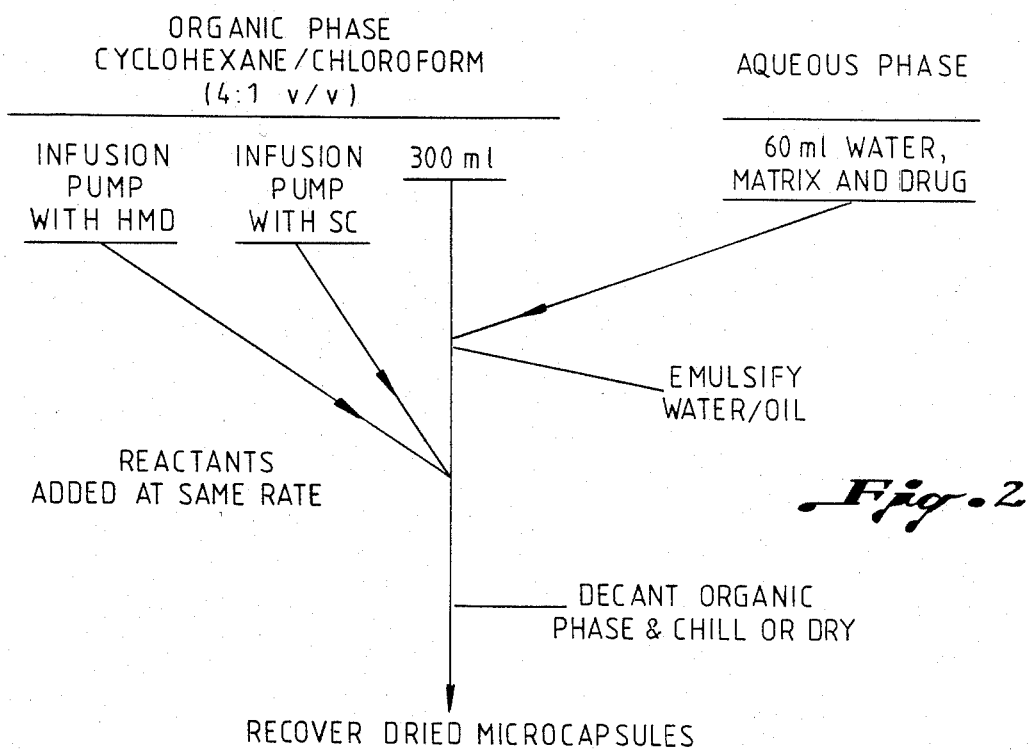
FIG. 2 represents a general schematic for preparation of formalized gelatin microcapsules with a drug, by the methods of this invention.

FIG. 2 illustrates the preparation of nylon microcapsules containing a formaldehyde-crosslinked gelatin matrix by the methods of the present invention. A mechanically stabilized emulsion of 60 ml of aqueous media containing 5 gm of gelatin and 2.5 gm of drug selected from one of morphine sulfate, diphenhydramine hydrochloride, or methantheline bromide was formed in 300 ml of the organic solvent. The polycondensation reactants were both infused simultaneously at the same volume rate. The rates used were described in EXAMPLE IX. The gelatin was crosslinked by addition of 20 ml of formalin (formaldehyde 37%, U.S.P.).

Then, after a total of five minutes had passed since the initial addition of reactants had begun, the stirrer was stopped and the organic phase was immediately decanted from the microcapsules (it was not possible to remove more than about 90% of the organic solvent in this manner). This slurry was placed in an ice bath for 1 hour, then dried under a hood at room temperature.

The formalized gelatin microcapsules were also studied for the influence of rinsing with different solvents and for the effect of varying the time of chilling the microcapsules before drying. Immediately after preparation, the organic solvent was decanted from microcapsules as completely as possible. The batch of microcapsules was separated into three approximately equal portions. One portion was not rinsed, one was rinsed with 50 ml of chloroform and the other was rinsed with 50 ml of carbon tetrachloride. These were all dried under a hood at room temperature. Separate batches were also prepared and separated into three equal portions. One of the portions was not rinsed, one was rinsed with 50 ml of ether and the other portion was rinsed with 50 ml of cyclohexane. These were all placed under a hood and dried at room temperature. As these dried, aggregates were gently broken up with a spatula. Little difference was noted in the ease of recovery when the microcapsules were rinsed with the solvents described. There was no difference observed for microcapsules of different batches that were not rinsed. The microcapsules that were rinsed with ether were found to dry more rapidly than those rinsed with the other solvents or not rinsed. No doubt, this is because of the greater volatility of ether compared to the other solvents.

Assay of the microcapsules demonstrated recovery greater than 98% for morphine sulfate in microcapsules made from each matrix type and for the other drugs in the formaldehyde crosslinked gelatin matrix containing microcapsules.

The difference of recovery or morphine sulfate in the formalized gelatin microcapsules made by the prior method of McGinity et al. and 98–99% recovery in those prepared from the present method is significant. More impressive is the difference of the diphenhydramine hydrochloride recovery of 56% in prior methods and 98% recovery in the present method.

Previous attempts to microencapsulate quaternary compounds (methantheline bromide) had been unsuccessful. Therefore, it was rewarding to find that these were easily prepared with the present method. Furthermore, when the microcapsules were viewed under a microscope immediately after their preparation, the methantheline bromide microcapsules appeared to have the most uniform size distribution.

EXAMPLE XII

Calcium sulfate matrix-containing microcapsules were also prepared by the schematic shown in FIG. 2. An aqueous suspension was made to contain 10 gm calcium sulfate, 5 gm of morphine sulfate and sufficient water for a final volume of 20 ml. This was suspended in 300 ml of the organic solvent by stirring. The reactants were infused simultaneously at the same rate from two Harvard infusion pumps, each with a 50 ml glass syringe, as described in EXAMPLE IX. The SC concentration was 0.1125 M and the concentration of HMD was 0.08 M (this is the initial concentration in the syringe). After a total of 5 minutes from the initiation of the reaction, the stirrer was stopped and the organic solvent was decanted from the microcapsules. The microcapsules were left under a hood to dry, without any agitation for one week.

EXAMPLE XIII

Calcium alginate matrix-containing microcapsules were prepared as illustrated in FIG. 2. A total of 60 ml of aqueous media was prepared to contain 2.5 gm of sodium alginate and 1.25 gm of morphine sulfate. The aqueous media was mechanically emulsified in 300 ml of the organic solvent. The reactants were added in two separate 50 ml volumes, using infusion pumps as described in EXAMPLE IX. The SC concentration was 0.1125 M and the HMD concentration was 0.08 M (each is given for the 50 ml volume). After the reactants were added, 5 ml of saturated aqueous $CaC_2$ solution was added. The reaction was continued for a total of 5 minutes, then the stirrer was stopped and the microcapsules were separated by decanting the organic solvent. The microcapsules were dried under a hood at room temperature.

The calcium alginate and calcium sulfate microcapsules were easily recovered as individual particles. The calcium alginate microcapsules required a moderate amount of attention to insure that the aggregates were broken up as the microcapsules dried. However, the calcium sulfate microcapsules did not require any attention for one week. After this time, they were broken up gently with a spatula and yielded free-flowing, spherical particles very easily. The calcium sulfate and formalized gelatin microcapsules were of approximately the same size. However, the calcium alginate microcapsules appeared to be several times the size of the others.

EXAMPLE XIV

Because the cost of organic solvents and problems associated with their disposal are real problems in terms of large scale production, a potential method to recover and recycle the organic solvent was developed. The solvent was washed twice in one fourth of its volume of 0.1 N HCl, then twice in one fourth of its volume of 0.1 N HCl with ten percent (v/v) ethanol. This was followed by one wash of 0.1 N aqueous NaOH and two washings of pure water. One experiment was performed using this method on a volume of the organic solvent (chloroform/cyclohexane, 1:4) and the same solvent was used to prepare four batches of microcapsules by the SAR method. The solvent was treated as described between each use. There was no difference observed in any of the microcapsules of any of the batches.

While the methods of this invention have been described in terms of preferred embodiments, it will be apparent to those of skill in the art that various changes may be made with the methods described without departing from the scope of the invention, which is defined by the following claims.

What is claimed is:

1. A process for the encapsulation of a hydrophilic core material in a membrane formed by interfacial polycondensation, the process comprising:
   in a first step, dispersing in a first continuous hydrophobic phase a hydrophilic phase comprising in solution the hydrophilic material to be encapsulated and a hydrophilic solvent or water; and then
   in a second stage, adding separately to the dispersion either sequentially or simultaneously, each of two complementary polycondensation monomer reactants:

the first polycondensation monomer reactant comprising a hydrophobic solvent-soluble reagent;

the second polycondensation monomer reactant comprising a hydrophilic solvent-soluble reagent dispersed in a second continuous hydrophobic phase;

allowing the polycondensation monomers to react, the reaction effective to cause interfacial polymerization of a membrane encapsulating the hydrophilic phase containing the hydrophilic core material; and separating the encapsulated material from the continuous hydrophobic phase.

2. The process according to claim 1 wherein the hydrophilic core comprises water soluble salts of anionic, cationic, quaternary, amphoteric or nonionic compounds.

3. The process according to claim 1 wherein the first or second continuous hydrophobic phase is a solution of cyclohexane and chloroform.

4. The process according to claim 1 wherein the first polycondensation monomer is selected from the group consisting of multifunctional acid halides, diacids, diisocyanates, multifunctional sulfonyl halides, and mixtures thereof.

5. The process according to claim 1 wherein the first polycondensation monomer is a multifunctional acid halide.

6. The process according to claim 5 wherein the multifunctional acid halide is sebacyl chloride.

7. The process according to claim 1 wherein the second polycondensation monomer reactant is selected from the group consisting of polyfunctional amines, polyols, diamines, and diols, and mixtures thereof dispersed in a hydrophobic continuous phase.

8. The process according to claim 1 wherein the second polycondensation monomer reactant is a diamine.

9. The process according to claim 8 wherein the diamine is hexamethylenediamine.

10. The process according to claim 1 wherein both the first and second polycondensation monomer reactants are added simultaneously to the first dispersion.

* * * * *